United States Patent [19]
Anders et al.

[11] Patent Number: 6,022,553
[45] Date of Patent: Feb. 8, 2000

[54] METHOD OF MAKING A BLOOD-COMPATIBLE ANTIMICROBIAL SURFACE

[75] Inventors: Christine Anders, Haltern; Guenter Lorenz, Marl; Hartwig Hoecker, Aachen, all of Germany

[73] Assignee: Huels Aktiengesellschaft, Marl, Germany

[21] Appl. No.: 09/063,412

[22] Filed: Apr. 21, 1998

[30] Foreign Application Priority Data

Apr. 21, 1997 [DE] Germany .................. 197 16 606

[51] Int. Cl.[7] .............. A01N 25/34; A61F 2/02; B05D 3/06; B05D 3/00
[52] U.S. Cl. ................ 424/411; 424/364; 424/404; 424/412; 424/422; 424/423; 424/429; 427/2.1; 427/2.24; 427/2.28; 427/2.3; 427/299; 427/535; 427/536; 428/411.1; 351/160 H; 623/1; 623/2; 623/11; 604/265
[58] Field of Search .................. 427/536, 538, 427/2.1, 2.12, 2.13, 2.24, 2.25, 2.3, 535, 569, 532, 299, 377, 387, 444, 2.28; 623/1, 2, 11; 351/160 H; 424/411, 404, 422, 423, 412, 429, 364; 604/265; 428/411.1, 409

[56] References Cited

U.S. PATENT DOCUMENTS

| | | | |
|---|---|---|---|
| 4,261,806 | 4/1981 | Asai et al. | 427/409 |
| 4,373,009 | 2/1983 | Winn | 427/412.1 |
| 4,601,911 | 7/1986 | Ueno et al. | 427/538 |
| 4,656,083 | 4/1987 | Hoffman et al. | 427/490 |
| 4,967,763 | 11/1990 | Nugent et al. | 128/763 |
| 5,028,453 | 7/1991 | Jeffrey et al. | 427/538 |
| 5,128,170 | 7/1992 | Matsusda et al. | 427/520 |
| 5,254,372 | 10/1993 | Nichols | 427/2.31 |
| 5,258,127 | 11/1993 | Gsell et al. | 427/569 |
| 5,312,642 | 5/1994 | Chesterfield et al. | 427/2.31 |
| 5,318,806 | 6/1994 | Montgomery et al. | 427/491 |
| 5,344,611 | 9/1994 | Vogler et al. | 422/101 |
| 5,415,819 | 5/1995 | Tisack | 427/536 |
| 5,447,756 | 9/1995 | Kamen | 427/489 |
| 5,453,467 | 9/1995 | Bamford et al. | 427/2.24 |
| 5,804,263 | 9/1998 | Goldberg et al. | 428/34.7 |
| 5,807,636 | 9/1998 | Sheu et al. | 428/403 |

FOREIGN PATENT DOCUMENTS

WO 92/18098 10/1992 WIPO .
WO 94/17904 8/1994 WIPO .

OTHER PUBLICATIONS

"Surface characterization and ex vivo blood compatibility study of plasma–modified small diameter tubing: effect of sulphur dioxide and hexamethyl–disiloxane plasmas." Jui–Che, Lin, et al., Biomaterials, 1995, vol. 16 No. 13 pp. 1017–1023. (No month).

"Staphylococcal Adherence to Modified Synthetic Polymer Surfaces" Proceedings of the 7th International Symposium, Stockholm, Jun. 29–Jul. 3, 1992, W. Kohnen, et al., pp. 408–410.

"Macromolecular Prodrugs" Prog. Polym Sci., vol. 20, pp. 211–257, 1995 Tatsuro Ouchi, et al. (No month).

"A novel antimicrobial central venous catheter impregnated with benzalkonium chloride," S. E. Tebbs, et al., Journal of Antimicrobial Chemotherapy (1993) 31, 261–271 (no month).

German Patent Application, 197 000 81.9, {w/English Abstract}(no date).

*Primary Examiner*—Diana Dudash
*Attorney, Agent, or Firm*—Oblon, Spivak, McClelland, Maier & Neustadt, P.C.

[57] ABSTRACT

A method for making antimicrobial, blood-compatible surfaces is provided, articles having surfaces made by this method, and the use of these articles in fields where controlling the spread of microbes and blood-compatibility are important. Such fields include the medical field, where it is critical to eliminate infection causing microbes and reduce the number of dangerous blood clots in patients.

20 Claims, No Drawings

METHOD OF MAKING A BLOOD-COMPATIBLE ANTIMICROBIAL SURFACE

BACKGROUND OF THE INVENTION

1. Field of the Invention

The present invention relates to a method of making blood-compatible, antimicrobial surfaces.

2. Description of the Related Art

Microbial growth can pose serious threats to human health. Microbes able to grow on the surfaces of medical articles can put patients at risk for developing uncontrollable infections. Increasing numbers of antibiotic resistant microbes are creating an urgent need to develop methods of inhibiting microbial growth on surfaces.

The rapidly growing biotechnology industry is especially sensitive to the dangers of microbial contamination and growth. In the laboratory, uncontrolled microbial growth can contaminate experiments and ruin their results. In a pharmaceutical plant, unwanted microbial growth in a reactor can taint drugs and disrupt production.

Microbial growth can also cause damage to our food and water supplies. Foods that are not properly stored in microbe free containers will quickly spoil, and perhaps even become poisonous. Pathogenic microbes found in raw foods, especially meats, spread on the surfaces of food handling articles creating a health hazard. Such food handling articles include utensils, dishes, glasses, bowls, cutting surfaces, and counter tops. Microbial growth in our water supplies not only threatens public health, but also clogs the pipes, pumps, and water treatment plants used to deliver safe drinking water.

Microbial growth on the surfaces of articles touched by many people promotes the spread of infectious diseases. Mundane articles such as seats, telephones, doorknobs, handles, latches, railings, and especially sinks and toilets, would be more sanitary if their surfaces were made to inhibit microbial growth.

There have been previous attempts to inhibit microbial growth on surfaces. Lacquer-like coatings containing quaternary ammonium salts have been applied as antimicrobial coating on surfaces (S. E. Tebbs and T. S. J. Elliott . J. Microbiol. Chemoth. 31 (1993). 261–271 the content of which is hereby incorporated by reference). Lacquers of silver salts have also been used for antimicrobial coatings (International Patent Application WO 92/18098. Unfortunately, the salts in these coatings are water soluble, and are quickly washed out of the coating by perspiration and other bodily fluids. Once the salts are removed, the coating looses its antimicrobial properties.

There have been attempts to chemically bond bactericidal active compounds on polymer surfaces (T. Ouchi and Y. Ohya, Progr. Polym. Sci. 20 (1995), 211. et seq,. Unfortunately, the chemical bonding of the antimicrobial compound to the polymer usually reduces its antimicrobial activity. Moreover, microbial debris has been found to build up on the surface of these treated polymers, eventually forming a layer thick enough to support new microbial growth.

It has been reported that polyurethane film can be treated to resist the microbe *Staphylococcus epidermidis*. The film is first pretreated with a glow discharge in the presence of oxygen, and then acrylic acid is grafted onto the film (W. Kohnen et al., ZBI. Bakt. Suppl. 26, 1994, pp. 408–410, Gustav Fischer Verlag, Stuttgart-Jena-New York.

In addition to being susceptible to microbial contamination, medical articles used as implants can cause dangerous blood clots. The clots are started when blood cells and other blood particles, such as thrombocytes, adhere to the surface of the implanted device. While certain disinfectants (e.g. benzalkonium chloride/heparin) have been shown to reduce the incidence of clotting, they have poor adherence to the underlying substrate, and quickly dissolve off the surface of the implanted device.

It has been reported that membranes treated with a low pressure plasma are less likely to cause blood clotting, i.e. be thrombogenic, than similar, untreated membranes (International Patent Application WO 94/17904. In the description of the treatment method, $SO_2$ was mentioned as a suitable plasma forming gas.

There have been additional reports on using $SO_2$ as a plasma forming gas in the plasma treatment of LDPE tubes (J. C. Lin et al., Biomaterials 16 (1995), 1017–1023. The authors reported that the surfaces modified by $SO_2$ plasma treatment were strongly hydrophilic, and more thrombogenic than untreated surfaces. They attributed this result to the addition of polar sulfonate groups, created by the $SO_2$ plasma treatment, to the already hydrophilic surface of the LOPE tubes.

SUMMARY OF THE INVENTION

Accordingly, one object of this invention is to provide a method for treating surfaces so that they are resistant to microbial growth and are preferably blood-compatible. Another object of the invention provides for treated articles having antimicrobial, preferably blood-compatible, surfaces. A further object of the invention provides for using these treated articles in fields where it is important for articles to have antimicrobial and/or blood-compatible surfaces.

These and other objects of the present invention have been satisfied by the surprising discovery that a hydrophilic substrate surface can be treated with an $SO_2$ plasma to make the surface antimicrobial and blood-compatible.

DETAILED DESCRIPTION OF THE PREFERRED EMBODIMENT

Within the context of the present invention, treated surfaces have reduced adhesion to microbes and increased resistance to microbial growth compared to similar, untreated surfaces. The term microbe is defined to include a wide variety of microorganisms including bacteria, yeasts, fungi, blood and tissue cells and particles found in blood, such as thrombocytes. Bacteria that are particularly affected by this surface treatment include *Staphylococcus aureus, Staphylococcus epidermidis, Streptococcus pyogenes, Klebsiella pneumoniae, Pseudomonas aeruginosa,* and *Escherichia coli.*

The treated surfaces are preferably free of monomer and oligomer components that are extractable and/or capable of migrating across the surface. Preferably, no toxic byproducts are released from the surface following treatment.

The polymeric plastic substrates suitable for the method according to the invention include hydrophilic homo- and copolymers, such as polyolefins, halogen-containing polymers, polymers and copolymers of vinylaromatic monomers, polycondensates, polyamides, polyether block amides, polyurethanes, polyethers, polycarbonates, polysulfones, polyetherketones, polyesteramides and -imides, polyacrylonitrile, polyacrylates, and polymethacrylates. Polyolefins include polyethylene, polyproplyene, polyisobutylene, polybutadiene, polyisoprene, natural rubbers, and polyethlene-coproplyene. Halogen-containing polymers include polyvinyl chloride, polyvinylidene chloride, polychloroprene, polytetrafluoroethylene, and polyvinylidene fluoride. Polymers and copolymers of vinylaromatic monomers include polystyrene, polyvinyltoluene, polystyrene-co-vinyl-toluene, polystyrene-co-acrylonitrile, polystyrene co-butadiene co-acrylonitrile. Polycondensates include polyesters like polyethylene terephthalate, and polybutylene terephthalate. Polyamides include polycaprolactam, polyaurolactam, and the polycondensate of adipic acid and hexamethylenediamine. Polyether block amides include laurolactam or caprolactam and polyethylene glycol having, on average, 8, 12 or 16 ethoxy groups.

The polymers used in the present invention should have a contact angle at 25 (with water that is less than 30° including 25°, 20°, 15° and 5° and less (as measured by the method of R. J. Good et al., Techniques of Measuring Contact Angles in Surface and Colloid Sciences, Vol. 11, Plenum Press New York, 1979. Polymers or copolymers having a contact angle of more than 30° are not adequately hydrophilic.

Polymers having inadequate hydrophilization can be treated by several methods to become adequately hydrophilic. For example, monomers containing hydroxyl groups, such as hydroxethyl (meth)acrylate or hydroxybutyl acrylate, can be grafted by radiation-induced means onto the polymer substrate (German Patent Application 19 000 79.7 the content of which is hereby incorporated by reference). Copolymers containing hydroxyl groups have also been used as alternatives to monomers (German Patent Application 197 000 81.9. These compounds are applied to the substrate surface typically by spraying, spin coating, and other conventional coating techniques. Other methods of making the polymers adequately hydrophilic include treating the polymers with argon plasma, ammonia plasma, irradiation with UV light between 150 and 320 nm, and etching with strong acids like sulfuric acid, hydrochloric acid, and nitric acid, and strong bases like alkali metal hydroxides.

The method of making antimicrobial, blood compatible surfaces according to the present invention involves exposing an adequately hydrophilic polymer to an sulfur dioxide plasma. When the treatment starts, the $SO_2$ should have a partial pressure of 10 to 100 Pa, preferably 10 to 40 Pa including 90, 80, 70, 60, 50, 40, 30, 20 and 15 Pa and all values, ranges and subranges therebetween. In a preferred embodiment, the atmosphere surrounding the substrate is evacuated and $SO_2$ is introduced without any other gases.

The $SO_2$ gas can be excited to form a plasma using any conventional method, including microwave energy. The power of the microwaves irradiating the $SO_2$ should be between 100 to 4000 watts, preferably between 400 to 2000 watts including 200, 300, 400, 500, 600, 700, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900, 4,000 and all values, ranges and subranges therebetween. The temperature of the plasma should be between 50 to 100° C., preferably between 50 and 70° C. The treatment period usually lasts between 1 second and 10 minutes, preferably between 10 seconds and 4 minutes.

Gases besides $SO_2$ may also be present during the treatment process, provided that they do not reduce the antimicrobial and blood clotting properties of the treated surface. These gases include the noble gases like argon, and nitrogen.

The treated surfaces can be analyzed using ESCA (Electron Spectroscopy for Chemical Applications) and SIMS (Secondary Ion Mass Spectroscopy). ESCA determines the total sulfur content deposited on the substrate surface, while SIMS can determine the relative amounts of sulfonate and sulfate groups on the treated surface. These techniques, and others, are also used to analyze the amount of carboxyl and hydroxyl groups that are on the treated surface.

Article surfaces treated by the method of the present invention are suitable for use in a wide variety of fields where antibacterial and/or anticlotting surfaces are required. They are useful in fields including food handling, hygiene, nutrition, pharmacology, and microbiology.

Articles having surfaces treated by the method of the present invention are useful as food handling utensils, dishes, glasses, bowls, cutting surfaces, and counter tops.

Articles having surfaces treated by the method of the present invention are especially useful for medical research and treatment. Such articles include a wide variety of therapeutic and diagnostic medical devices, including catheters, stents, dialysis tubes, catheter tubes, drainage tubes, artificial blood vessels, cardiac valves, artificial limbs, dental prostheses, contact lenses, and surgical materials. These articles also include articles useful for pharmaceutical research and manufacturing where equipment including containers, pipelines, bottles, pipettes, packaging articles and dispatch articles, that must be nearly free of microbes.

Articles having surfaces treated by the method of the present invention are also useful when the articles are handled by many people such as seats, telephones, doorknobs, handles, latches, railings, and especially sinks and toilets.

Articles according to the invention may be treated with $SO_2$ plasma by creating such a plasma at the desired surfaces of said article, or such articles can be made from raw materials which have been subjected to the $SO_2$ plasma of the invention.

EXAMPLES

Having generally described this invention, a further understanding can be obtained by reference to certain specific examples that are provided herein for purposes of illustration only and not intended to be limiting unless otherwise specified. All percentages are by weight, unless stated other vise.

I. Preparation of the Antimicrobial, Blood-Compatible Surfaces a. Selecting the Plastic Films The films in Table 1 were treated by the method of the present invention. There thicknesses were between 0.1 to 0.5 mm and surfaces areas around 4 $cm^2$. The films were made by several methods including dissolving powders, pouring the solution into a Petri dish, and evaporating the solvent to leave behind the plastic film. Alternatively, films were made by calendering or extrusion of the starting materials. In some instances, the films were available from the manufacturer.

TABLE 1

Films employed

| Film No. | Plastic | Name, Source | Preparation |
|---|---|---|---|
| F 1 | Polyamide 12 | VESTAMID, HÜLS AG | Extruding |
| F 2 | Polystyrene | VESTYRON, HÜLS AG | Pressing |

TABLE 1-continued

Films employed

| Film No. | Plastic | Name, Source | Preparation |
|---|---|---|---|
| F 3 | Polyurethane | Pellethane 2363-A, DOW CHEMICAL COMPANY | Extruding |
| F 4 | Polyether block amide | VESTAMID, HÜLS AG | Extruding |
| F 5 | Polyethylene | VESTOLEN A, VESTOLEN GmbH | Extruding |
| F 6 | Polypropylene | VESTOLEN P, VESTOLEN GmbH | Extruding |
| F 7 | Polyorganosiloxane | NG 37-52, Silicon GmbH, Nünchritz | Knife application |
| F 8 | Polyvinyl chloride | VESTOLIT P + DEHP, VESTOLIT GmbH | Brabender application |
| F 9 | Polytetrafluoroethylene | HOSTAFLON, HOECHST AG | Extruding | b. Activation of the film surface

The films in Table 1 were activated according to the methods and conditions indicated in Table 2, prior to being exposed to the $SO_2$ plasma.

TABLE 2

Activation conditions

| Activation number | Activation method | Conditions |
|---|---|---|
| A 1 | UV excimer radiation (= 172 nm) | 1 s-20 min, 1 mbar, 4 cm distance |
| A 2 | Microwave plasma (argon) | 1 s-30 min 1 mbar |
| A 3 | High frequency plasma (argon) | 1 s-30 min 6 mbar |
| A 4 | Corona | 0.1 s-60 s, 2 mm distance |
| A 5 | Flaming | $CH_4$: air = 1:10.4 cm distance |
| A 6 | Gamma irradiation | 1 MRad |
| A 7 | Electron beams | 1 min |
| A 8 | NaOH soltition | 1%, 5 min, 60° C. |
| A 9 | UV excimer radiation (= 308 nm) | 10 s-20 min | c. Graft copolymerization of the activated films

After activation the films were coated with 5% aqueous solutions of monomers selected from Table 3.

TABLE 3

Monomers in 5% aqueous solutions

| Monomer | Abbreviation |
|---|---|
| Acrylic acid | AAc |
| Methacrylic acid | MAAc |
| Diethylene glycol methacrylate | DEGMA |
| Polyethylene glycol methacrylate | PEGMA |
| 2-Hydroxyethyl methacrylate | HEMA |
| 2-Hydroxyethyl acrylate | HEA |
| 4-Hydroxybutyl acrylate | HBA |

The monomer solutions were coated onto the activated films by a method selected from Table 4.

TABLE 4

Coating methods

| Coating number | Coating method |
|---|---|
| T 1 | Immersion |
| T 2 | Spraying |
| T 3 | Spreading |

During immersion and after spraying or spreading, the films or articles were irradiated with UV light in the range 250–500 nm, preferably 290–320 nm.

d. $SO_2$ plasma treatment of hydrophilized polymer surfaces

The hydrophilized polymer surfaces were then finished with $SO_2$ groups by an $SO_2$ plasma treatment. The samples were subjected to an $SO_2$ plasma treatment in a microwave plasma unit at a pressure of 10 to 40 Pa and at a power of the microwave generator of 100 to 4000 watts, in particular between 300 and 2000 watts, for 10 seconds to 4 minutes. The sulfur content of the treated surface was determined by ESCA. The results of the treatment of the present invention on polyamide 12 (F1). polyurethane (F2) and polyether block amide (F4) are shown in Table 5.

TABLE 5

ESCA sulfur content in atom % of hydorphilized polymer surfaces after $SO_2$ plasma treatment for varying periods of time

| Treatment time/sample | F1/AAc | F1/MAAc | F1/DEGMA | F1/PEGMA | F1/HEMA | F1/HEA | F1/HBA |
|---|---|---|---|---|---|---|---|
| 10 s | 0.6 | 0.9 | 0.9 | 1.3 | 1.2 | 1.3 | 1.0 |
| 60 s | 2.2 | 3.0 | 3.8 | 3.9 | 3.6 | 1.9 | 1.2 |
| 240 s | 4.2 | 4.0 | 5.0 | 5.2 | 5.0 | 3.7 | 2.2 |

| | F3/AAc | F3/MAAc | F3/DEGMA | F3/PEGMA | F3/HEMA | F3/HEA | F3/HBA |
|---|---|---|---|---|---|---|---|
| 10 s | 1.0 | 1.1 | 1.1 | 1.5 | 1.4 | 0.0 | 1.1 |
| 60 s | 2.5 | 3.1 | 3.8 | 3.5 | 3.4 | 2.1 | 1.9 |
| 240 s | 4.0 | 4.2 | 5.1 | 4.9 | 5.2 | 4.5 | 2.5 |

TABLE 5-continued

ESCA sulfur content in atom % of hydrophilized polymer surfaces
after $SO_2$ plasma treatment for varying periods of time

| | F4/AAc | F4/MAAc | F4/DEGMA | F4/PEGMA | F4/HEMA | F4/HEA | F4/HBA |
|---|---|---|---|---|---|---|---|
| 10 s | 1.3 | 0.6 | 1.1 | 1.0 | 1.4 | 1.1 | 0.9 |
| 60 s | 2.9 | 3.0 | 4.0 | 3.1 | 3.0 | 2.7 | 2.2 |
| 240 s | 4.5 | 3.9 | 5.1 | 4.5 | 4.7 | 4.9 | 3.1 |

II. Determination of Antimicrobial properties

Microbe adhesion to surfaces treated by the method of the present invention was determined for four strains of bacteria typically found in infected medical devices, such as catheters. The bacteria are listed in Table 6.

TABLE 6

Bacterial strains used in adhesion measurements of treated surfaces

| | Strain |
|---|---|
| B 1 | *Staphylococcus aureus* |
| B 2 | *Staphylococcus epidermidis* |
| B 3 | *Escherichia coli* |
| B 4 | *Klebsiella pneumoniae* |

Microbe adhesion measurements were complicated by the fact that a single microbe can multiply quickly into dozens of microbes on a surface. Primary adhesion measurements reflect the number of microbes adhering to a surface before the microbes had multiplied. In these examples, primary adhesion measurements were performed.

The subsequent adhesion measurements described below were made on the *Klebsiella pneumonias* bacteria. Primary adhesion measurements for the other bacterial strains (B1 to B3) were made in a similar fashion.

a. Determination of primary bacterial adhesion under static conditions

An overnight culture of the bacterial strain *Klebsiella pneumoniae* in yeast extract-pep/one-glucose nutrient medium ( 1%+1%+1%) was centrifuged off and taken up again in phosphate-buffered saline (=PBS; 0.05 M $KH_2PO_4$, pH 7.2–0.9% NaCl). It was diluted to a cell concentration of 108 cells/ml in PBS buffer. The suspended bacteria were brought into contact with the piece of film for 3 hours. To do this, circular pieces of film that had a diameter of 1.6 cm (=4.02 $cm^2$) were coated on both sides, pinned to a dissecting needle, and shaken with the cell suspension. The films, having been coated on one side in the form of a disk, 4.5 cm in diameter, were combined with a 2–3 mm thick supporting membrane of soft PVC, and clamped into a membrane filter apparatus. The cell suspension was added to the side of the film pointing upwards and was shaken for 3 hours. During the shaking, it was critical that the membrane filter apparatus be sealed, and no cell suspension leak out of the apparatus.

Following the shaking, the bacterial suspension was aspirated with a water-jet pump, and then the pieces of film were shaken with 20 ml of sterile PBS solution in a 100 ml beaker for 2 minutes. The film was again immersed in sterile PBS solution and then extracted in a boiling water bath in 10 ml of heated TRIS/EDTA (0.1 M trishydroxyethyl-aminomethane 4 mM ethylenediaminetetraacetic acid, adjusted to pH 7.8 using HCl) for 2 minutes.

Small Eppendorf cups were filled with the extraction solution and frozen immediately at −20° C. until bioluminescence determination of the extracted adenosinetriphosphate (ATP). The determination was carried out as follows: 100 ml of reagent mix (bioluminescence test CLS II, BOEHRINGER MANNHEIM GmbH) were added to a transparent polycarbonate tube and the light pulses were integrated over a 10 second period in the light pulse measuring apparatus LUMAT LB 9501 (Laboratorien Prof. Berthold GmbH, Wildbad). A 100 μl sample was then added and measured again. The relative light units (RLU) were obtained by subtracting the number of light pulses in the reagent mix from the number of light pulses measured in the complete mixture. This value was related to the number of bacteria adhering to the film. The conversion factor between the RLU value and bacterial count was determined by extracting an aliquot of 0.1 ml of the bacterial suspension containing 108 cells per ml in 10 ml of hot TRIS/EDTA and then determining the ATP content.

For *Klebsiella pneumoniae*, there was a value of $1.74 \times 10^4$ RLU which converted to $1 \times 10^7$ cells in the ATP extraction mixture. $4.7 \times 10^4$ RLU was measured for the 4 $cm^2$ film, so the number of microbes per $cm^2$ of film surface was:

$$\frac{4.7 \cdot 10^4}{4}$$

=$1.175 \cdot 10^4$ RLU/$cm^2$ $6.8 \times 10^6$ microbes per $cm^2$ $6.8 \times 10^6$/$cm^2$ *Klebsiella pneumoniae* microbes adhered to the film surface.

Reduced microbe adhesion for the $SO_2$ plasma-treated hydrophilized polymer surfaces of the present invention were shown for polyamide 12 (F1) in Table 7.

TABLE 7

Bacterial adhesion to hydrophilized and $SO_2$ plasma-treated polyamide 12 (F1)

| | $SO_2$ | Bacterial adhesion [10,000 cells/$cm^2$] | | | | | | |
|---|---|---|---|---|---|---|---|---|
| | plasma | B 1 | | B 2 | | B 3 | | B 4 | |
| Sample | treatment | Value | D[%] | Value | D[%] | Value | D[%] | Value | D[%] |
| F1 | Untreated | 380 | — | 450 | — | 680 | — | 770 | — |
| F1/AAc | 10 s | 41 | 89 | 51 | 89 | 20 | 97 | 50 | 98 |

TABLE 7-continued

Bacterial adhesion to hydrophilized and SO₂ plasma-treated polyamide 12 (F1)

| Sample | SO₂ plasma treatment | Bacterial adhesion [10,000 cells/cm²] | | | | | | | |
|---|---|---|---|---|---|---|---|---|---|
| | | B 1 | | B 2 | | B 3 | | B 4 | |
| | | Value | D[%] | Value | D[%] | Value | D[%] | Value | D[%] |
| F1/AAc | 60 s | 40 | 89 | 45 | 90 | 10 | 99 | 61 | 92 |
| F1/AAc | 240 s | 28 | 93 | 32 | 93 | 45 | 98 | 49 | 98 |
| F1/HEMA | 10 s | 51 | 87 | 71 | 84 | 41 | 95 | 95 | 90 |
| F1/HEMA | 60 s | 48 | 87 | 60 | 87 | 49 | 94 | 96 | 96 |
| F1/HEMA | 240 s | 45 | 88 | 65 | 86 | 43 | 94 | 105 | 86 |
| F1/PEGMA | 10 s | 30 | 92 | 33 | 93 | 41 | 94 | 150 | 81 |
| F1/PEGMA | 60 s | 41 | 89 | 25 | 94 | 38 | 94 | 90 | 88 |
| F1/PEGMA | 240 s | 25 | 93 | 28 | 94 | 35 | 95 | 39 | 95 |

D [%] = Difference from the untreated polyamide 12 (1 F) in % = Reduction of bacterial adhesion in %

D [%]=Difference from the untreated polyamide 12 (1 F) in % =Reduction of bacterial adhesion in %

Table 7 illustrates that films coated by the method according to the present invention had a considerable reduction in microbial adhesion. The decreases were clearly over 50% in comparison with the untreated substrate.

For a surface treated with the method of the present invention, microbial adhesion to the surface is reduced by 50% or more, preferably by 80% or more, more preferably by 90% or more, even more preferably by 99% or more compared to a surface that is otherwise identical except for not being treated by the method of the present invention.

III. Determination of blood compatibility for the treated surfaces

To assess the blood compatibility, various parameters were investigated. The investigations were carried out by an accredited test laboratory according to DIN EN 30993, the contents of which are hereby incorporated by reference.

a. C5a generation (complement activation)

The complement system was made up of more than 20 proteins that act as a defense system against invading microorganisms. On activation of the complement system connected with diseases or due to contact with synthetic surfaces, a cascade of proteolytic enzymes released the anaphylatoxins C3a, C4a and C5a. The increased concentration of a complement component indicated the activation of the complement system. Activation of the leucocytes and their aggregation could have been triggered as secondary processes. Table 8 shows the results of the testing of complement activation as exemplified by PA 12 (F1), F1/HEMA and F1/HBA, F1/HEMA and F1/HBA were treated with an SO₂ plasma for 240 seconds.

b. Determination of adherent and activated platelets

The adhesion and the activation of platelets on synthetic surfaces in contact with blood was regarded as a significant limitation for the use of plastics in the medical field. The results of the determination of adherent and activated platelets as exemplified by PA 12(F1). F1/HEMA and F1/HBA are indicated in Table 8.

Partial thromboplastin time (PTT)

The partial thromboplastin time (PTT) was the clotting time of recalcified citrate plasma after the addition of partial thromboplastin. A reduction of the PTT indicated activation of the clotting system, and formation of a thrombus. Blood-compatible materials showed no activation of the clotting system and therefore no reduction of the PTT.

TABLE 8

Complement activation, adherent platelets, activated, adherent platelets and partial thromboplastin time of PA 12 (F1), F1/HEMA and F1/HBA after blood contact; F1/HEMA and F1/HBA were treated with an SO₂ plasma for 240 s

| Sample | C5a generation in % relative control | Adherent platelets in % relative to the control | Activated adherent platelets in % relative to the control | Partial thromboplastin time in % relative to the control |
|---|---|---|---|---|
| Plasma | — | — | — | 100 |
| Control | 100* | 100$ | 100# | 80# |
| F1 | 24 | 80 | 100 | 107 |
| F1/HEMA/SO₂ | 20 | 56 | 31 | 103 |
| F1/HBA/SO₂ | 22 | 63 | 40 | 115 |

*Cellulose membrane;
$Polypropylene;
Kaolin-treated cephalin

Table 8 illustrates that, by the method according to the invention, polymeric SO - containing coatings were obtained that lead to a considerable improvement in blood compatibility. This was demonstrated quite clearly for the treated surfaces in their platelet adhesion and the activation of adherent platelets.

For a surface treated with the method of the present invention, the number of adherent platelets on the surface, measured as above, is reduced to 90% or less, preferably to 60% or less, more preferably to 50% or less, even more preferably to 40% or less of the number of adherent platelets on a surface that is otherwise identical except for not being treated by the method of the present invention.

Furthermore, a surface treated with the method of the present invention has a reduction in the relative number of activated adherent platelets measured at the surface of at least 5%, preferably at least 10%, preferably at least 30%, more preferably at least 50%, compared to a surface that is otherwise identical except for not being treated by the method of the present invention.

The present application is based on German Priority Application 197 16 606.7, filed with the German Patent Office on Apr. 21, 1997, the entire contents of which are hereby incorporated by reference.

Obviously, numerous modifications and variations of the present invention are possible in light of the above teachings. It is therefore to be understood that within the scope of the appended claims, the invention may be practiced otherwise than as specifically described herein.

What is claimed is:

1. A method for forming a bacteria-repelling and blood-compatible modified surface on a substrate, comprising the sequential steps of:

a. activating the surface of a substrate;

b. grafting the resulting activated surface of the substrate with a hydrophilic monomer, and c. subjecting the resulting grafted substrate to an $SO_2$ plasma treatment, whereby bacterial adhesion and blood platelet adhesion to said modified surface after exposure to said plasma treatment is less than prior to said plasma treatment.

2. The method as claimed in claim 1, wherein the number of platelets that adhere to said surface after said exposure to said plasma is reduced to 50% or less of the number of platelets that adhere to the surface prior to exposure to said plasma.

3. The method as claimed in claim 1, wherein the number of platelets that adhere to said surface after said exposure to said plasma is reduced to 60% or less of the number of platelets that adhere to the surface prior to exposure to said plasma.

4. The method as claimed in claim 1, wherein the number of platelets that are activated on said surface after said exposure to said plasma is reduced to 40% or less of the number of platelets that are activated on the surface prior to exposure to said plasma.

5. The method as claimed in claim 1, wherein the number of platelets that are activated on said surface after said exposure to said plasma is reduced to 50% or less of the number of platelets that are activated on the surface prior to exposure to said plasma.

6. The method as claimed in claim 1, wherein the $SO_2$ gas partial pressure in said plasma is 10 to 100 Pa.

7. The method as claimed in claim 1, wherein the $SO_2$ gas partial pressure in said plasma is 10 to 40 Pa.

8. The method as claimed in claim 1, wherein the $SO_2$ gas is excited by microwave energy to form said plasma.

9. The method as claimed in claim 1, wherein said surface is exposed to said plasma for 1 second to 10 minutes.

10. The method as claimed in claim 1, wherein said surface is exposed to said plasma for 10 seconds to 4 minutes.

11. The method as claimed in claim 1 wherein the number of microbes that adhere to said surface after said exposure to said plasma is reduced by 99% or more compared to the number of microbes that adhere to the surface prior to exposure to said plasma.

12. An article made by the method of claim 11.

13. The article according to claim 12, wherein said article is selected from the group consisting of food handling articles, biomedical articles, and waste treatment articles.

14. The article according to claim 12, wherein said article is selected from the group consisting of seats, telephones, doorknobs, handles, latches, railings, sinks, and toilets.

15. The article according to claim 12, wherein said article is selected from the group consisting of catheters, stents, dialysis tubes, catheter tubes, drainage tubes, artificial blood vessels, cardiac valves, artificial limbs, dental prostheses, contact lenses, and surgical suture material.

16. The article according to claim 12, wherein said article is selected from the group consisting of utensils, glasses, bowls, cutting surfaces, and counter tops.

17. The method as claimed in claim 1, wherein said hydrophilic monomer is acrylic acid, methacrylic acid, diethylene glycol methacrylate, polyethylene glycol methacrylate, 2-hyroxyethyl acrylate, 2-hydroxyethyl acrylate or 4-hydroxybutyl acrylate.

18. The method as claimed in claim 1, wherein the number of microbes that adhere to said surface after said exposure to said plasma is reduced by 80% or more compared to the number of microbes that adhere to the surface prior to exposure to said plasma.

19. The method as claimed in claim 18, wherein said microbes are selected from the group consisting of *Staphylococcus aureus, Staphylococcus epidermidis, Escherichia coli*, and *Kelbsiella pneumoniae.*

20. The method according to claim 1, wherein said substrate surface is selected from the group consisting of polyolefins, halogen-containing polymers, polymers and copolymers of vinylaromatic monomers, polycondensates, polyamides, polyether block amides, polyurethanes, polyethers, polycarbonates, polysulfones, polyetherketones, polyesteramides and -imides, polyacrylonitrile, polyacrylates, and polymethacrylates.

* * * * *